(12) United States Patent
Kovi et al.

(10) Patent No.: US 11,857,677 B2
(45) Date of Patent: Jan. 2, 2024

(54) READY TO USE INJECTABLE FORMULATIONS OF MELPHALAN AND PROCESSES FOR PREPARATION THEREOF

(71) Applicant: RK Pharma Solutions LLC, Piscataway, NJ (US)

(72) Inventors: Ravishanker Kovi, Monroe Township, NJ (US); Jayaraman Kannappan, Vadodara (IN); Thupalli Ajeykumar Reddy, Bangalore (IN); Vamshi Yekkanti, Telangana (IN); Raghu Kasu, Monmouth Jct, NJ (US)

(73) Assignee: RK PHARMA INC., Pearl River, NY (US)

( * ) Notice: Subject to any disclaimer, the term of this patent is extended or adjusted under 35 U.S.C. 154(b) by 0 days.

(21) Appl. No.: 17/124,668

(22) Filed: Dec. 17, 2020

(65) Prior Publication Data
US 2021/0205216 A1 Jul. 8, 2021

(30) Foreign Application Priority Data

Dec. 19, 2019 (IN) .............................. 201921052782

(51) Int. Cl.
| | |
|---|---|
| *A61K 9/08* | (2006.01) |
| *A61K 9/00* | (2006.01) |
| *A61K 31/198* | (2006.01) |
| *A61K 47/10* | (2017.01) |
| *A61K 47/18* | (2017.01) |
| *A61K 47/32* | (2006.01) |

(52) U.S. Cl.
CPC .............. *A61K 9/08* (2013.01); *A61K 9/0019* (2013.01); *A61K 31/198* (2013.01); *A61K 47/10* (2013.01); *A61K 47/183* (2013.01); *A61K 47/32* (2013.01)

(58) Field of Classification Search
None
See application file for complete search history.

(56) References Cited

U.S. PATENT DOCUMENTS

2010/0311838 A1* 12/2010 Pipkin ..................... A61P 35/00
514/564
2018/0193255 A1* 7/2018 Chandrashekhar .... A61K 47/10

OTHER PUBLICATIONS

Flora et al. "Chelation in Metal Intoxication" "Ethylenediaminetetraacetic Acid" Int. J. Environ. Res. Public Health 2010.*

* cited by examiner

*Primary Examiner* — Danah Al-Awadi
(74) *Attorney, Agent, or Firm* — Antonio Papageorgiou; Lombard & Geliebter LLP

(57) ABSTRACT

The present application provides stable ready-to-use injectable formulations of melphalan, methods for preparing storage-stable, ready-to-use injectable formulations that include melphalan, which are easy to administer without need of any reconstitution step and has a desirable solubility, stability, and safety profile. In other embodiments, provided are storage-stable, ready-to-use, injectable liquid parenteral formulations that include melphalan and other pharmaceutically acceptable excipients.

1 Claim, No Drawings

READY TO USE INJECTABLE FORMULATIONS OF MELPHALAN AND PROCESSES FOR PREPARATION THEREOF

BACKGROUND

The present application relates to liquid pharmaceutical formulations of melphalan with enhanced stability against degradation. The present application also provides storage-stable ready-to-use injectable formulations of melphalan and processes for the preparation of the formulations.

Melphalan, known chemically as 4-[bis(2-chloroethyl)amino]-L-phenylalanine, is a bifunctional alkylating agent that is active against selected human neoplastic diseases. The molecular formula is $C_{13}H_{18}Cl_2N_2O_2$ with a molecular weight of 305.20. The structural formula is:

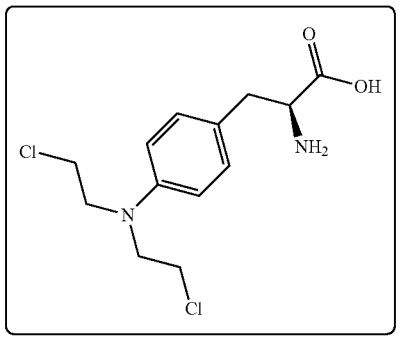 [SMILES: N[C@@H](Cc1ccc(N(CCCl)CCCl)cc1)C(=O)O]

Melphalan was first synthesized in 1953 by Bergel and Stock. Melphalan is practically insoluble in water and has a pKa1 of ~2.5.

The commercial formulation of injectable melphalan (ALKERAN® for Injection, ApoPharma) is supplied as a sterile, nonpyrogenic, freeze-dried lyophilized powder. Each single-use vial contains melphalan hydrochloride equivalent to 50 mg melphalan and 20 mg povidone. Prior to administration, ALKERAN® for Injection must be reconstituted using a sterile diluent provided therewith. The sterile diluent contains sodium citrate 0.2 g, propylene glycol 6.0 mL, ethanol (96%) 0.52 mL, and water. To reconstitute, 10 ml of the diluent is injected directly into the vial of lyophilized powder and the vial is shaken to obtain a clear 5 mg/l solution of melphalan. ALKERAN® for Injection is then administered intravenously.

ALKERAN® for Injection has certain disadvantages. Care must be taken during the initial dilution to prevent foaming. The reconstituted final drug solution of ALKERAN® for Injection is stable only for a short period of time. For example, in a time as short as 30 minutes the reconstituted melphalan may begin to degrade. Improper reconstitution may sometimes result in failure to provide a clear solution.

SUMMARY

Embodiments of the methods disclosed herein provide a storage-stable, ready-to-use injectable formulation including melphalan which is easy to administer without need of any reconstitution step and has a desirable solubility, stability and safety profile.

In one or more embodiments, there is provided a storage-stable ready-to-use liquid parenteral formulation of melphalan.

In other embodiments, provided are storage-stable, ready-to-use, injectable liquid parenteral formulations including melphalan and other pharmaceutically acceptable excipients.

The storage stable, ready-to-use, injectable formulations are useful for palliative treatment of patients with multiple myeloma for whom oral therapy is not appropriate.

In one aspect, a method for preparing a ready-to-use injectable melphalan formulation is provided that includes: adding melphalan to a vessel containing at least one pharmaceutical acceptable solvent to form a melphalan solution; optionally adjusting the pH of the solution; and filling at least one vial with the pH melphalan solution, wherein the pH melphalan solution is storage-stable.

In at least one embodiment, the weight percentage of the melphalan in the solution is from about 0.2% to about 0.8%.

In at least one embodiment, the weight percentage of the melphalan to the one or more solvents is from about 0.4% to about 0.6%.

In at least one embodiment, the formulation includes a plurality of solvents.

In at least one embodiment, the plurality of solvents are selected from a group consisting of propylene glycol (PG), polyethylene glycol (PEG), ethanol, and water.

In at least one embodiment, the method includes adding and mixing a chelating agent to the at least one solvent, wherein the chelating agent is mixed with the at least one solvent before adding the melphalan, therewith forming a chelating agent solution.

In at least one embodiment, the chelating agent comprises EDTA and wherein the weight percentage of the EDTA to the one or more solvents is from about 0.1% to about 2%.

In at least one embodiment, the weight percentage of the EDTA to the one or more solvents is from about 1% to about 1.5%.

In at least one embodiment, the method includes adding povidone to the chelating agent solution.

In at least one embodiment, the povidone and melphalan are added to the chelating agent solution and wherein the weight percentage of the povidone and melphalan in the chelating agent solution is from about 0.2% to about 2%.

In at least one embodiment, the weight percentage of the povidone and melphalan in the chelating agent solution is from 0.5% to about 1.5%.

In at least one embodiment, the method includes adding a surfactant in a sufficient amount to clarify the melphalan solution.

In at least one embodiment, the pH of the solution is adjusted from about 3.5 to about 5.5 or from about 7.5 to about 9.0.

In at least one embodiment, the melphalan formulation has a purity of at least 90 at 25° C./60% RH for a period of 43 days.

In at least one embodiment, the melphalan formulation has a purity of at least 99 after 50 days.

In at least one embodiment, the melphalan formulation has a purity of at least 99 after 5 months of storage at 2-8° C.

In at least one aspect, a storage-stable ready-to-use injectable melphalan formulation is provided that includes melphalan and at least one pharmaceutical acceptable solvent.

In at least one embodiment, the melphalan formulation has a purity of at least 90 at 25° C./60% RH for a period of 43 days.

In at least one embodiment, the melphalan formulation has a purity of 99 after 50 days.

In at least one embodiment, the melphalan formulation has a purity of at least 99 after 5 months of storage at 2-8° C.

The details of one or more embodiments of the invention are set forth in the description below. Other features, objects and advantages of the invention will be apparent from the description.

DETAILED DESCRIPTION OF THE PREFERRED EMBODIMENTS

Various embodiments will now be described more fully hereinafter with reference to the accompanying examples and experiments, in which illustrative embodiments of the invention are shown. The novel concepts may, however, be embodied in many different forms and should not be construed as limited to the embodiments set forth herein; rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein "melphalan" refers to the pharmaceutically acceptable salts, solvates, hydrates and anhydrous forms thereof. The examples herein all refer to melphalan hydrochloride, but the invention is not limited in this regards.

As used herein "ready-to-use" when used in connection with a melphalan formulation refers to a formulation that includes melphalan, optionally including one or more pharmaceutically acceptable excipients, in the form of a solution, suspension or emulsion, wherein the formulation does not require any reconstitution or dilution with parenterally acceptable diluent and can be directly administered to the patient.

As used herein, the phrases "ready-to-dilute" and "concentrate ready for dilution" refer to any liquid formulation of melphalan, optionally including one or more pharmaceutically acceptable excipients, in the form of a solution, suspension or emulsion, in which the liquid formulation can be diluted with a suitable diluent for parenteral administration before administering to the patient.

As used herein, the term "storage-stable" refers to any liquid melphalan-containing formulation having sufficient physical and chemical stability to allow storage at a convenient temperature and relative humidity (RH), such as from about 0° C. to about 60° C. and about 20% to 75% RH, for a reasonable period of time. "Physical stability" refers to maintenance of colour or colourless state, dissolved oxygen level, head space oxygen level and particulate matter and "chemical stability" relates to formation of drug-related impurities in terms of total impurities, single maximum individual impurity, or maximum individual unknown impurity. For pharmaceutical products, stability is required for commercially relevant times after manufacturing, such as for about 6, 12, 18, 24, or 36 months, during which time a product is kept in its original packaging under specified storage conditions. In one embodiment a liquid melphalan formulation may be considered storage-stable if after a predetermined period of time, such as but not limited to one week, at least one month, at least three months, at least six months, at least one year, or at least 2 years, no precipitation is observed, the composition remains clear and has sufficient chemical stability to permit safe administration to a patient.

The term "parenteral" or "injectable" refers to routes selected from subcutaneous (SC), intravenous (IV), intramuscular (IM), intradermal (ID), intraperitoneal (IP) and the like.

The ready-to-use or ready-to-dilute formulations disclosed herein may be formulated as aqueous or non-aqueous solutions, suspensions, or emulsions.

The ready-to-use parenteral formulations disclosed herein include melphalan, preferably melphalan hydrochloride, and one or more pharmaceutically acceptable solvents, cosolvents and/or solubilizing agents. In other embodiments, ready-to-use liquid parenteral formulations of melphalan include melphalan, one or more pharmaceutically acceptable solvents, co-solvents, and/or solubilizing agents, and one or more pharmaceutically acceptable excipients such as but are not limited to surfactants, wetting agents, emulsifiers, preservatives, chelating agents, antioxidants, polymers, antifoaming agents, buffering agents, pH adjusting agents, channel forming agents, osmotic adjustment agents and the like and mixtures thereof.

Suitable pharmaceutically acceptable solvents include but are not limited to water, water immiscible solvents, water miscible solvents, oily components, hydrophilic solvents, and hydrophobic solvents. Specific examples of pharmaceutically acceptable solvents include but are not limited to dimethylacetamide (DMA), dimethyl sulfoxide (DMSO), N-methylpyrolidone, dimethylisosorbide, ethanol, propylene glycol, glycerine, polyethylene alcohol, propylene glycol esters, polyethylene glycols and the like. Preferred solvents are dimethylacetamide (DMA), ethanol, polyethylene glycols (PEG), glycerine, benzyl alcohol and propylene glycol.

Suitable pharmaceutically acceptable co-solvents include but are not limited to ethanol, polyethylene glycol, glycerine, polyethylene glycol and glycofurol.

Suitable pharmaceutically acceptable solubilizing agents include but are not limited to cyclodextrin derivatives, alpha-cyclodextrin, beta-cyclodextrin, for example, hydroxypropyl beta cyclodextrin (HPBCD), sulfobutylether-betacyclodextrin, randomly methylated beta-cyclodextrin and the like, gamma-cyclodextrin, modified alpha-cyclodextrin, modified beta cyclodextrin, modified gamma cyclodextrin or any combination thereof.

Examples of pharmaceutically acceptable surfactants include but are not limited to amphoteric, non-ionic, cationic and anionic molecules. For example, suitable surfactants include but are not limited to polysorbates, sodium lauryl sulfate, lauryl dimethyl amine oxide, docusate sodium, cetyl trimethyl ammonium bromide (CTAB), polyethoxylated alcohols, polyoxyethylene sorbitan, octoxynol, polyoxyl lauryl ether, Brij® surfactants (polyoxyethylene vegetable-based fatty ethers derived from lauryl, cetyl, stearyl and oleyl alcohols), bile salts (such as sodium deoxycholate and sodium cholate), polyoxyl castor oil, nonylphenol ethoxylate, lecithin, polyoxyethylene surfactants, polyethylene glycol esters, glycol esters of fatty acids, monoalkanolamine condensates, polyoxyethylene fatty acid amides, quaternary ammonium salts, polyoxyethylene alkyl and alicyclic amines, polyoxyethylene, sorbitan monolaurate, sorbitan stearate, Cremophor® (polyethoxylated castor oil), Solutol® (ethylene oxide/12-hydroxy stearic acid), tyloxapol, etc. and combinations thereof.

Examples of pharmaceutically acceptable wetting agents include but are not limited to sulphate, sulphonate, carboxylates, ethoxylates, alkylphenol ethoxlates, esters of glycerol, esters of sorbitol, amine oxides, sulphoxides, phosphine oxides and combinations thereof.

Examples of pharmaceutically acceptable emulsifiers include but are not limited to soybean oil, safflower oil, sesame oil, castor oil, lecithin, PEG-PE, Pluronic, sorbitol, xylitol, tocopherol, deferoxamine mesylate, benzyl alcohol and combinations thereof.

Examples of pharmaceutically acceptable preservatives include but are not limited to chlorobutanol, benzalkonium chloride, methyl paraben, propyl paraben, benzoic acid, sodium benzoate, sorbic acid, benzethonium chloride, cetyl pyridinium chloride, benzyl bromide, benzyl alcohol, phenylmercury nitrate, phenylmercury acetate, thiomersal, merthiolate, chlorhexidine, phenylethyl alcohol, quaternary ammonium chloride, sodium benzoate, sodium propionate, etc. and combinations thereof.

Pharmaceutically acceptable chelating agents include but are not limited to citric acid and derivatives thereof, for example, anhydrous citric acid and the like, ethylenediaminetetraacetic acid (EDTA), disodium EDTA or derivatives thereof, niacinamide or derivatives thereof, sodium deoxycholate or derivatives thereof, pentetic acid or derivatives thereof, etc. and combination thereof.

Examples of pharmaceutically acceptable anti-oxidants include but are not limited to butylated hydroxytoluene (BHT), butylated hydroxyanisole (BHA), propyl gallate (PG), monothioglycerol, ascorbic acid, sodium ascorbate, erythorbic acid, potassium metabisulfite, sodium metabisulfite, propionic acid, sodium formaldehyde sulphoxylate, reduced glutathione, thiourea, cysteine, n-acetylcysteine, methionine, sodium sulfite, alkyl gallate, vitamin E or other tocopherol analogs such as tocopherol acetate and TPGS, etc. and combinations thereof.

Examples of pharmaceutically acceptable polymers include but are not limited to carbomer, polycarbophil, gellan gum, cellulose derivatives, acrylates, etc. and combinations thereof.

Examples of pharmaceutically acceptable anti-foaming agents include but are not limited to alkyl polyacrylates, castor oil, fatty acids, fatty acid esters, fatty acid sulphates, fatty alcohol, fatty alcohol esters, olive oil, paraffin oil, silicone oil, paraffin wax and combinations thereof.

Examples of pharmaceutically acceptable buffering agents include but are not limited to hydrochloric acid, citrate buffer, acetate buffer, Sorensens's phosphate buffer, sodium bicarbonate, sodium carbonate, sodium hydroxide, and combinations thereof.

Examples of pharmaceutically acceptable pH adjusting agents include but are not limited to sodium hydroxide, hydrochloric acid, boric acid, citric acid, acetic acid, phosphoric acid, succinic acid, potassium hydroxide, ammonium hydroxide, magnesium oxide, calcium carbonate, magnesium carbonate, magnesium aluminum silicates, malic acid, potassium citrate, sodium phosphate, lactic acid, gluconic acid, tartaric acid, fumaric acid, diethanolamine, monoethanolamine, sodium carbonate, sodium bicarbonate, triethanolamine, etc. and combinations thereof.

Examples of pharmaceutically acceptable osmotic adjustment agents include but are not limited to sodium chloride, potassium chloride, calcium chloride and magnesium chloride, glucose, glycerol, etc. and combinations thereof.

Generally, a process for preparing formulations of melphalan and the resulting formulations are provided. The process generally involves first adding melphalan to a vessel containing a mixture of one or more solvents, to form a melphalan solution. In a preferred embodiment, the weight % of melphalan I the solution is between about 0.2% to about 0.8%, or more preferably about 0.4% to about 0.6%. In at least one embodiment, a plurality of solvents are used, such as, propylene glycol (PG) polyethylene glycol (PEG) and ethanol, or water and ethanol, or any combination thereof. In some embodiments, a chelating agent, such as EDTA, is mixed with the one or more solvents, at a weight % of from about 0.1% to about 2%, or more preferably from about 1% to about 1.5%, and the melphalan is added to the chelating agent solution. In some embodiments, povidone is added to the solution with the melphalan, at a weight % from about 0.2% to about 2%, or more preferably from about 0.5% to about 1.5%.

Optionally, a sufficient amount of Polaxomer 188 or other surfactants may be added to clarify the solution. The pH of the solution may be adjusted, using an appropriate buffering agent, from about 3.0 to about 6.0, or more preferably about 3.5 to about 5.5. In certain embodiments, the pH of the solution may be adjusted from about 7.0 to about 9.5, or more preferably from about 7.5 to about 9.0. Suitable pharmaceutically acceptable solvents may then be added to make up the volume of the solution. The resulting solution may be filtered and used to fill vials for parenteral administration. The resulting formulation has a purity of at least 90 at 25° C./60% RH for a period of 43 days, or preferably at least 99 after 50 days, or more preferably at least 99 after 5 months of storage at 2-8° C.

EXAMPLES

The following examples are for the illustration of the invention only and are not intended in any way to limit the scope of the present invention.

Example 1

TABLE 1

| Ingredients | Qty/vial |
| --- | --- |
| Melphalan | 50 mg |
| Poloxamer 188 | 5 mg |
| Polyethylene glycol (PEG) | 4 ml |
| Ethanol | 6 ml |
| 0.1N HCl | QS |

Melphalan was added to a manufacturing vessel containing a mixture of solvents polyethylene glycol (PEG) and ethanol. Polaxomer 188 was added to obtain a clear solution. pH was adjusted to 3.5-5.5 using 0.1N HCl. Volume was made up using a mixture of PEG and ethanol. The obtained solution was filtered and filled in vials followed by capping and sealing. The melphalan formulation was tested for stability at 25° C./60% RH for a period of 43 days. Stability data is summarized in Table 1A.

TABLE 1A

| Stability at Day 43 | Day 43 |
|---|---|
| Purity | 90.41 |
| Maximum Individual Impurity | 3.3 |
| Total Impurities | 9.59 |

Example 2

TABLE 2

| Ingredients | Qty/vial |
|---|---|
| Melphalan | 50 |
| EDTA | 10 mg |
| Water for injection (WFI) | 1 ml |
| Ethanol | 9 ml |
| 0.1N HCl | QS |

EDTA was dissolved in water and added to a manufacturing vessel containing a mixture of ethanol and water to obtain a clear solution. Melphalan was added to the above solution mixture. pH was adjusted to 3.5-5.5 using 0.1N HCl. Volume was made up using water and ethanol. The obtained solution was filtered and filled in vials followed by capping and sealing. The formulation was tested for stability at 25° C./60% RH for a period of 43 days. Stability data is summarized in Table 2A.

TABLE 2A

| Stability at Day 43 | Day 43 |
|---|---|
| Purity | 91.81 |
| Maximum Individual Impurity | 3.01 |
| Total Impurities | 8.2 |

Example 3

TABLE 3

| Ingredients | Qty/vial |
|---|---|
| Melphalan | 50 mg |
| EDTA | 5 mg |
| PEG | 5 ml |
| Water | 0.2 ml |
| Ethanol | 4.8 ml |
| 0.1N HCl | QS |

EDTA was dissolved in water and added to a manufacturing vessel containing a mixture of PEG and ethanol to obtain a clear solution. Melphalan was added to the above solution mixture. pH was adjusted to 3.5-5.5 using 0.1N HCl. Volume was made up using PEG and ethanol. The obtained solution was filtered and filled in vials followed by capping and sealing. The formulation was tested for stability at 2-8° C. for a period of 50 days. Stability data is summarized in Table 3A.

TABLE 3A

| Stability at Day 50 | Day 50 |
|---|---|
| Purity | 99.48 |
| Maximum Individual Impurity | 0.12 |
| Total Impurities | 0.52 |

Example 4

TABLE 4

| Ingredients | Qty/vial |
|---|---|
| Melphalan | 50 mg |
| EDTA | 5 mg |
| PEG | 2 ml |
| Water | 0.4 ml |
| Ethanol | 7.6 ml |
| 0.1N HCl | QS |

EDTA was dissolved in water and added to a manufacturing vessel containing a mixture of PEG and ethanol to obtain a clear solution. Melphalan was added to the above solution mixture. pH was adjusted to 3.5-5.5 using 0.1N HCl. Volume was made up using mixture of PEG and ethanol. The obtained solution was filtered and filled in vials followed by capping and sealing. The formulation was tested for stability at 2-8° C. for a period of 5 months. Stability data is summarized in Table 4A.

TABLE 4A

| Stability at 5 Months | 5 Months |
|---|---|
| Purity | 99.05 |
| Maximum Individual impurity | 0.25 |
| Total Impurities | 0.95 |

Example 5

TABLE 5

| Ingredients | Qty/vial |
|---|---|
| Melphalan | 50 mg |
| Povidone | 5 mg |
| EDTA | 5 mg |
| PEG | 5 ml |
| Water | 0.2 ml |
| Ethanol | 4.8 ml |
| 0.1N HCl | QS |

EDTA was dissolved in water and added to a manufacturing vessel containing a mixture of PEG and ethanol. Melphalan and povidone were added to the above solution mixture. pH was adjusted to 3.5-5.5 using 0.1N HCl. Volume was made up using mixture of PEG and ethanol. The obtained solution was filtered and filled in vials followed by capping and sealing. The formulation was tested for stability at 25° C./60% RH for a period of 22 days. Stability data is summarized in Table 5A.

TABLE 5A

| Stability at Day 22 | Day 22 |
|---|---|
| Purity | 92.04 |
| Maximum Individual Impurity | 1.76 |
| Total Impurities | 7.96 |

Example 6

TABLE 6

| Ingredients | Qty/vial |
|---|---|
| Melphalan | 50 mg |
| Povidone | 5 mg |
| EDTA | 5 mg |
| Propylene glycol (PG) | 5 ml |
| Water | 0.2 ml |
| Ethanol | 4.8 ml |
| 0.1N HCl | QS |

EDTA was dissolved in water and added to a manufacturing vessel containing a mixture of PG and ethanol. Melphalan and povidone were added to the above mixture. pH was adjusted to 3.5-5.5 using 0.1N HCl. Volume was made up using PG and ethanol. The obtained solution was filtered and filled in vials followed by capping and sealing. The formulation was tested for stability at 25° C./60% RH for a period of 22 days. Stability data is summarized in Table 6A.

TABLE 6A

| Stability at Day 22 | Day 22 |
|---|---|
| Purity | 93.62 |
| Maximum Individual Impurity | 1.66 |
| Total Impurities | 6.38 |

Example 7

TABLE 7

| Ingredients | Qty/vial |
|---|---|
| Melphalan | 50 mg |
| Povidone | 5 mg |
| EDTA | 5 mg |
| PG | 5 ml |
| Water | 0.2 ml |
| Ethanol | 4.8 ml |
| 0.1N NaOH | QS |

EDTA and povidone was dissolved in water and added to a manufacturing vessel containing a mixture of PG and ethanol. Melphalan and povidone were added to the above solution mixture. pH was adjusted to 7.5-9.0 using 0.1 N NaOH. Volume was made up using PG and ethanol. The obtained solution was filtered and filled in vials followed by capping and sealing. The formulation was tested for stability at 25° C./60% RH for a period of 22 days. Stability data is summarized in Table 7A.

TABLE 7A

| Stability at Day 22 | Day 22 |
|---|---|
| Purity | 92.79 |
| Maximum Individual Impurity | 1.82 |
| Total Impurities | 7.21 |

Example 8

TABLE 8

| Ingredients | Qty/vial |
|---|---|
| Melphalan | 50 mg |
| Povidone | 5 mg |
| EDTA | 5 mg |
| PEG | 5 ml |
| Water | 0.2 ml |
| Ethanol | 4.8 ml |
| 0.1N NaOH | QS |

EDTA and povidone were dissolved in water and added to a manufacturing vessel containing a mixture of PEG and ethanol. Melphalan was added to the above solution mixture. pH was adjusted between pH 7.5-9.0 using 0.1N NaOH. Volume was made up using PEG and ethanol. The obtained solution was filtered and filled in vials followed by capping and sealing. The formulation was tested for stability at 25° C./60% RH for a period of 22 days. Stability data is summarized in Table 8A.

TABLE 8A

| Stability at Day 22 | Day 22 |
|---|---|
| Purity | 88.36 |
| Maximum Individual impurity | 3.00 |
| Total Impurities | 11.64 |

Example 9

TABLE 9

| Ingredients | Qty/vial |
|---|---|
| Melphalan | 50 mg |
| EDTA | 5 mg |
| PG | 1 ml |
| Water | 0.2 ml |
| Ethanol | 8.8 ml |
| 0.1N NaOH | QS |

EDTA was dissolved in water and added to a manufacturing vessel containing a mixture of PG and ethanol. Melphalan was added to the above solution mixture. pH was adjusted between pH 3.5-5.5 using 0.1N HCl. Volume was made up using PG and ethanol. The obtained solution was filtered and filled in vials followed by capping and sealing. The formulation was tested for stability at 2-8° C. for a period of 22 days. Stability data is summarized in Table 9A.

TABLE 9A

| Stability at Day 22 | Day 22 |
| --- | --- |
| Purity | 92.79 |
| Maximum Individual impurity | 1.82 |
| Total Impurities | 7.2 |

Example 10

TABLE 10

| Ingredients | Qty/vial |
| --- | --- |
| Melphalan | 50 mg |
| EDTA | 5 mg |
| PG | 1 ml |
| Water | 0.2 ml |
| Benzyl alcohol | 8.8 ml |
| 0.1N NaOH/0.1N HCL | QS |

EDTA was dissolved in water and added to a manufacturing vessel containing a mixture of PG and benzyl alcohol. Melphalan was added to the above solution mixture. pH was adjusted between pH 3.5-5.5 using 0.1N HCl/0.1N NaOH. Volume was made up using PG and benzyl alcohol. The obtained solution was filtered and filled in vials followed by capping and sealing. The formulation was tested for stability at 2-8° C. for a period of 22 days. Stability data is summarized in Table 10A.

TABLE 10A

| Stability at Day 22 | Day 22 |
| --- | --- |
| Purity | 99.38 |
| Maximum Individual impurity | 0.38 |
| Total Impurities | 0.62 |

Example 11

TABLE 11

| Ingredients | Qty/vial |
| --- | --- |
| Melphalan | 50 mg |
| EDTA | 5 mg |
| PG | 2 ml |
| Water | 0.4 ml |
| Ethanol | 7.6 ml |
| 0.1N NaOH/0.1N HCL | QS |

EDTA was dissolved in water and added to a manufacturing vessel containing PG. 80% of Ethanol was added to above solution. Melphalan was added to the above solution mixture. pH was adjusted between pH 3.5-5.5 using 0.1N NaOH/0.1N HCL. Volume was made up using remaining quantity of Ethanol. The obtained solution was filtered and filled in vials followed by capping and sealing. The formulation was tested for stability at 2-8° C. for a period of 6 Months. Stability data is summarized in Table 11A.

TABLE 11A

| Stability at 6 Months | 14 months |
| --- | --- |
| Purity | 99.03 |
| Maximum Individual impurity | 0.21 |
| Total Impurities | 0.97 |

Example 12

TABLE 12

| Ingredients | Qty/vial |
| --- | --- |
| Melphalan | 50 mg |
| EDTA | 5 mg |
| PEG | 2 ml |
| Water | 0.4 ml |
| Ethanol | 7.6 ml |
| 0.1N NaOH/0.1N HCL | QS |

EDTA was dissolved in water and added to a manufacturing vessel containing PEG. 80% of ethanol was added to above solution. Melphalan was added to the above solution mixture. pH was adjusted between pH 3.5-5.5 using 0.1N NaOH/0.1N HCL. Volume was made up using remaining quantity of ethanol. The obtained solution was filtered and filled in vials followed by capping and sealing. The formulation was tested for stability at 2-8° C. for a period of 5 Months. Stability data is summarized in Table 12A.

TABLE 12A

| Stability at 5 Month | 5 Months |
| --- | --- |
| Purity | 99.05 |
| Maximum Individual impurity | 0.25 |
| Total Impurities | 0.95 |

Example 13

| Ingredients | Qty/vial |
| --- | --- |
| Melphalan | 50 mg |
| PG | 5 ml |
| Ethanol | 5 ml |
| 0.1N NaOH/0.1N HCL | QS |

NLT 80% of batch volume ethanol was transferred into a manufacturing vessel.

Propylene glycol was added to a vessel containing ethanol. Melphalan was added to the above mixture. Check the pH of the sample and if required adjust the pH to 3.5-5.5 using 0.1N NaOH/0.1N HCL. Final batch volume was made up using ethanol. The obtained solution was filtered and filled in vials followed by capping and sealing. The formulation was tested for stability at 2-8° C. for a period of 1 Month. Stability data is summarized 13A.

TABLE 13A

| Stability at 1 Month | 1 Month |
| --- | --- |
| Purity | 99.48 |
| Maximum Individual impurity | 0.1 |
| Total Impurities | 0.52 |

Although the formulations, compositions, schemes and methods of the present disclosure have been described with reference to exemplary embodiments thereof, the present disclosure is not limited thereby. Indeed, the exemplary embodiments are implementations of the disclosed methods are provided for illustrative and non-limitative purposes. Changes, modifications, enhancements and/or refinements to the disclosed methods may be made without departing from the spirit or scope of the present disclosure. Accordingly, such changes, modifications, enhancements and/or refinements are encompassed within the scope of the present invention. All publications, patent applications, patents, figures and other references mentioned herein are expressly incorporated by reference in their entirety.

What is claimed is:

1. A stable ready to use liquid parenteral formulation, consisting of 0.2 weight % to 0.8 weight % melphalan or its pharmaceutically acceptable salt, at least one pharmaceutically acceptable solvent selected from propylene glycol (PG), polyethylene glycol (PEG), ethanol, benzyl alcohol, and water, a buffer selected from 0.1N NaOH, 0.1N HCl or combination thereof and at least one pharmaceutically acceptable excipient or adjuvant selected from povidone or poloxamer.

* * * * *